US009169332B2

(12) United States Patent
Jin et al.

(10) Patent No.: US 9,169,332 B2
(45) Date of Patent: Oct. 27, 2015

(54) PHOTOPOLYMERIZABLE AND PHOTOCLEAVABLE RESINS AND LOW SHRINK AND LOW STRESS COMPOSITE COMPOSITIONS

(75) Inventors: Xiaoming D Jin, Middletown, DE (US); Paul D Hammesfahr, Lewes, DE (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 12/584,859

(22) Filed: Sep. 14, 2009

(65) Prior Publication Data

US 2010/0022709 A1  Jan. 28, 2010

Related U.S. Application Data

(63) Continuation of application No. 11/811,201, filed on Jun. 8, 2007, now abandoned.

(60) Provisional application No. 60/812,669, filed on Jun. 9, 2006.

(51) Int. Cl.
 *A61K 6/083* (2006.01)
 *C08F 2/48* (2006.01)
 *A61K 6/087* (2006.01)
 *C08F 222/10* (2006.01)

(52) U.S. Cl.
 CPC . *C08F 2/48* (2013.01); *A61K 6/083* (2013.01); *A61K 6/087* (2013.01); *C08F 222/1006* (2013.01)

(58) Field of Classification Search
 CPC .................................. A61K 6/083; C08F 2/48
 USPC .......................................... 522/162; 523/116
 See application file for complete search history.

(56) References Cited

U.S. PATENT DOCUMENTS

| | | | |
|---|---|---|---|
| 4,286,047 A * | 8/1981 | Bennett et al. | 522/31 |
| 5,600,035 A * | 2/1997 | Kahle et al. | 568/932 |
| 5,886,064 A | 3/1999 | Rheinberger et al. | |
| 6,315,566 B1 | 11/2001 | Shen et al. | |
| 6,767,955 B2 | 7/2004 | Jia | |
| 7,544,721 B2 | 6/2009 | Gaud et al. | |
| 2005/0182148 A1* | 8/2005 | Gaud et al. | 522/1 |
| 2005/0197422 A1* | 9/2005 | Mayadunne et al. | 523/105 |
| 2008/0076848 A1* | 3/2008 | Jin et al. | 522/162 |
| 2008/0076853 A1 | 3/2008 | Jin et al. | |

FOREIGN PATENT DOCUMENTS

| | | | |
|---|---|---|---|
| EP | 0282827 A2 | 9/1988 | |
| EP | 0373662 A2 | 6/1990 | |
| EP | 373662 A2 * | 6/1990 | C08F 2/50 |
| JP | 53099292 | 8/1978 | |
| WO | 03082218 A2 | 10/2003 | |
| WO | WO 03/082218 A2 * | 10/2003 | |
| WO | 2006044795 A2 | 4/2006 | |
| WO | 2007146239 A2 | 12/2007 | |

OTHER PUBLICATIONS

XP-002346645; Application of Diol Dimethacrylates in Dental Composites and Their Influence on Polymerization Shrinkage, Gogdal et al; Journal of Applied Polymer Science; vol. 66, 2333-2337(1997).

* cited by examiner

*Primary Examiner* — Michael Pepitone
(74) *Attorney, Agent, or Firm* — Leana Levin; Douglas J. Hura; David A. Zdurne

(57) ABSTRACT

A photopolymerizable and photocleavable (P&P) resin monomer is derived from a reactive photoresponsible moiety via various linkages to form photopolymerizable monomers and/or oligomers.

7 Claims, No Drawings

PHOTOPOLYMERIZABLE AND PHOTOCLEAVABLE RESINS AND LOW SHRINK AND LOW STRESS COMPOSITE COMPOSITIONS

FIELD OF THE INVENTION

This invention relates to photopolymerizable and photocleavable resin monomers and resin composite compositions, which feature by its unique balanced overall performance including very low polymerization shrinkage and very low shrinkage stress as well. The photoreactive moiety incorporated into such new resin's main frame enable to make the resin and/or the cured resin networks that are based upon such resin photocleavable. Thus the polymerization rate of free radical reaction for (meth) acrylate-based resin systems should be substantially reduced since it alters the network formation process and consequently allows the shrinkage stress to get relief significantly. In addition, it is expected that radically polymerizable resin systems containing such P&P resin would find wide range application in microelectronic, special coating and restorative dentistry where the dimensional stability and contraction stress within cured materials are critical to the total performance.

BACKGROUND OF THE INVENTION

Highly cross-linked polymers have been studied widely as matrices for composites, foamed structures, structural adhesives, insulators for electronic packaging, etc. The densely cross-linked structures are the basis of superior mechanical properties such as high modulus, high fracture strength, and solvent resistance. However, these materials are irreversibly damaged by high stress due to the formation and propagation of cracks. Polymerization stress is originated from polymerization shrinkage in combination with the limited chain mobility. Which eventually leads to contraction stress concentration and gradually such a trapped stress would be released and cause microscopic damage in the certain weak zone like interfacial areas. Macroscopically it was reflected as debonding, cracking, et al. Similarly, the origin of contraction stress in current adhesive restorations is also attributed to the restrained shrinkage while a resin composite is curing, which is also highly dependent on the configuration of the restoration. Furthermore, non-homogeneous deformations during functional loading can damage the interface as well as the coherence of the material. Various approaches have been explored by limiting the overall stress generation either from the restorative materials, or by minimizing a direct stress concentration at the restored interface. It included, for example, new resin, new resin chemistry, new filler, new curing process, new bonding agent, and even new procedure.

There has been tremendous attention paid to new resin matrix development that could offer low polymerization shrinkage and shrinkage stress. For example, various structure and geometry derivatives of (meth) acrylate-based resin systems; non-(meth) acrylates resin systems, non-radical-based resin system. In addition, for light curable, low shrink dental composites, not only new resin systems and new photinitiators, new filler and filter's surface modification have also been extensively explored, such as filler with various particle size and size distribution, from nanometer to micrometer, different shape, irregular as milled or spherical as-made. It can also be different in composition like inorganic, organic, hybrid. Although an incremental improvement has been achieved with each approach and/or their mutual contribution, polymerization stress is still the biggest challenge in cured network systems.

This invention is related to a new kind of resin composition. However, unlike conventional resin system, a new concept is involved in designing such a new resin composition, which would render the polymerization stress in post-gel stage to a subsequent, selective network cleavage in order to have the stress partially released. As mentioned above, all of previous arts towards low shrink and low stress are based on the limitation on the shrink and stress formation in general. However, the shrinkage and stress development in cured network system should have two different stages: a pre-gel phase and a post-gel phase. Actually, most efforts of current arts are focused on the pre-gel stage and some of them were proved to be effective. Unfortunately, these approaches become ineffective in terms to control the stress development in post-gel stage, where the shrinkage is not as much as in the pre-gel stage but the stress turns to much more sensitive to any polymerization extend. It is the immobility nature of the increasing cross-link density within the curing system that leads to the increasing stress concentration within the curing system, period. Even worse, the problem does not stop here and the trapped stress would eventually get relief from slow relaxation, which can create additional damage on a restored system. Therefore, our approach is based on such a concept that in the post-gel stage if some of "closed net" of any cross-linked system can be selectively broken to promote an extended stress relief period, the total stress concentration would be substantially reduced. To fulfill such a task, a photopolymerizable and photocleavable resin is proposed and a general molecular constitution is designed. It was expected that such a resin monomer can be polymerized like any other resin monomer can be polymerized like any other resin monomer but its mainframe is able to be triggered to break upon additional light source such as near UV is blended. This is a typical photocleavable process, but it is its capability to be photopolymerized and embedded into a cross-linked system that makes it unique. In addition, it also makes possible to avoid regenerating any leachable species through such secondary breakage.

Photocleavage is nothing new in solid synthesis of peptides, from which new peptides was directed on certain template in designed sequence, then it was cleaved from its template via a subsequent light exposure. There is no chemical contamination with such a process. On the other hand, photoacid and photobase could be viewed as extended applications for photocleavage. Acidic or basic component is temporally latent to avoid any unwanted interaction with others in the system and they can be released on demand such as light exposure to trigger the regeneration of the acid or base, which then act as normal acidic or basic catalyst for next step reactions. Recently, thermally removable or photo-chemically reversible materials are developed in order to make polymer or polymeric network depolymerizable or degradable for applications such as easily removing of fill-in polymer in MEMS, thermally labile adhesives, thermaspray coatings and removable encapsulation et al. Most recently, photocleavable dentrimers are explored in order to improve the efficiency for drug delivery. Based on our knowledge, there is no prior art involved photocleavable segment in cured network for contract stress control. However, all of those related arts could be used as a practical base to justify this investigation.

Scheme Illustration for Photopolymerizable & Photocleavable Resin and the Cure Network Therefrom
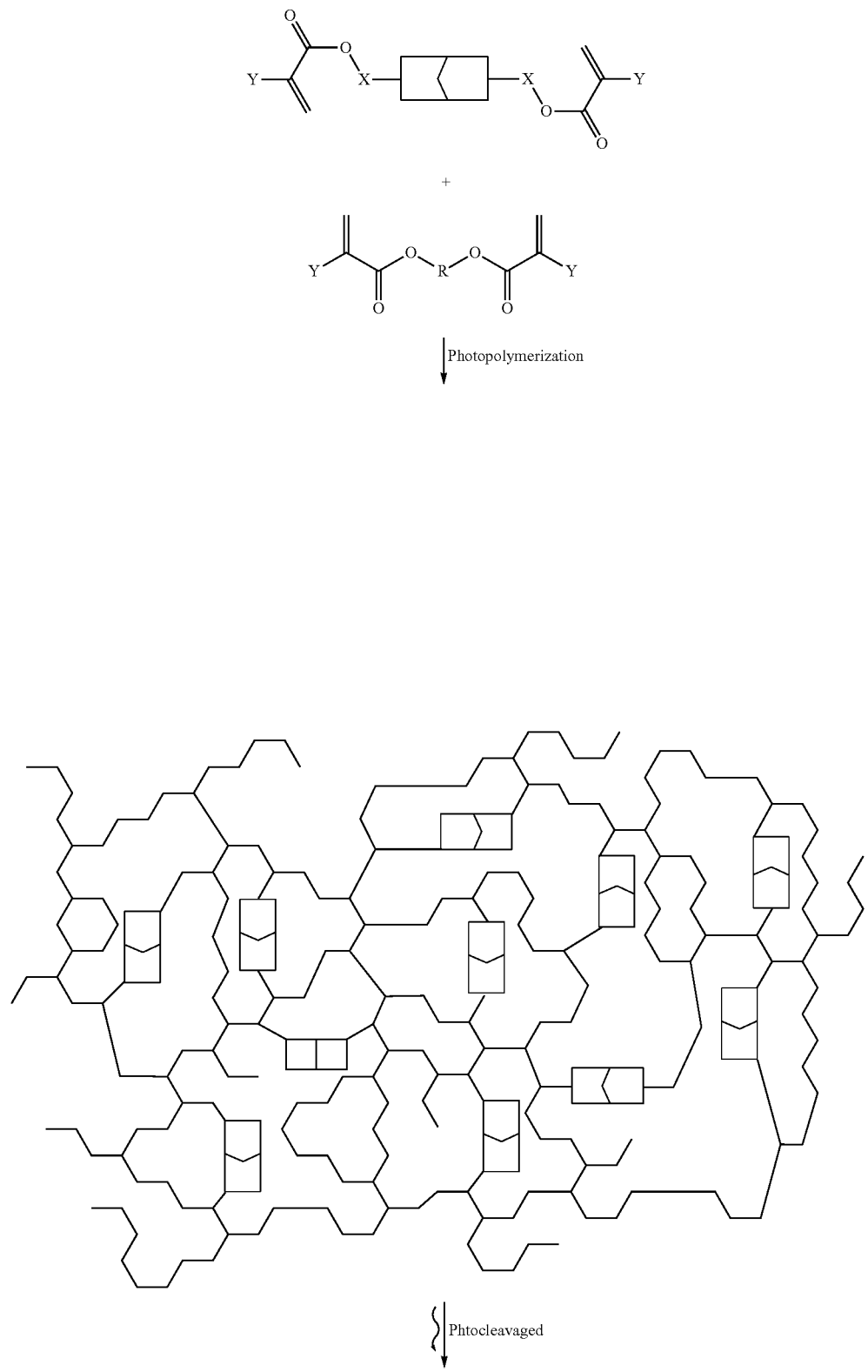

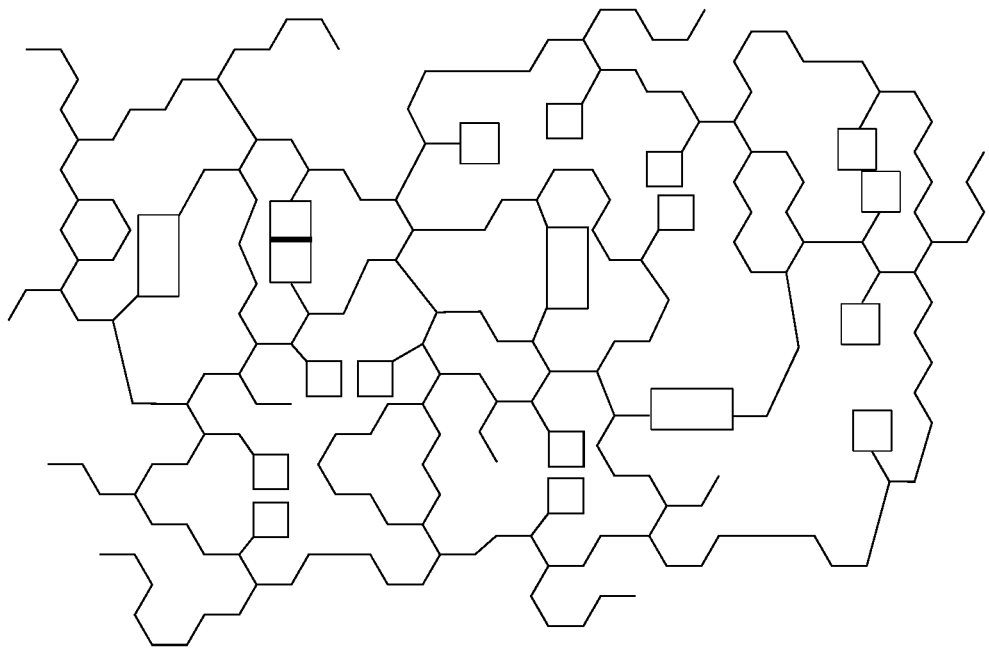

DESCRIPTION OF THE PREFERRED EMBODIMENTS

Theoretically speaking, if any kind of environmentally sensitive moiety, such as a thermally cleavable or photo-labile linkage were incorporated into polymerizable resin monomers, such resin or its resulting polymeric material would become command-responsible, more specifically enable them thermo-cleavable or photo-cleavable. The chemistry of some classical photo-initiators could be adopted as the base for designing such photopolymerizable and photocleavable resin monomers, because such an initiator was explored as polymerizable photoinitiator or macroinitiator. However, none of them were really incorporated into polymer chain or polymeric network to make the polymeric chain or network breakable one way or another.

It is another objective of this investigation to develop a new resin system for next generation low shrink and low stress restorative materials by incorporating a photocleavable or thermally liable moiety as part of a photopolymerizable resin monomer. It was expected with such an unusual approach it would enable a conventional polymerized network should be selectively cleavaged, thus to disperse the stress from post-polymerization and furthermore to result in a self stress-relief, ultimately to minimize the overall stress concentration.

In order to make a polymerized network cleavable-on-command by light or photocleavable, a light responsible moiety should be stable towards standard light exposure process such as visible light curing until additional exposure to specific light with distinguished energy level. In particular, such energy source can be anything other than the standard visible blue light. Near UV light would be on of typical examples among the many possible choices. Furthermore, it was expected that compounds derived from ortho-nitrobenzyl segment or from α-hydroxyalkylphenone should ideal candidates for this new class resin monomers that be photopolymerized by visible light and be triggered to be breakable by extra UV light if needed.

Scheme I: Typical Photopolymerizable and Photocleavable Resin Monomer Based on α-hydroxyalkylphenone

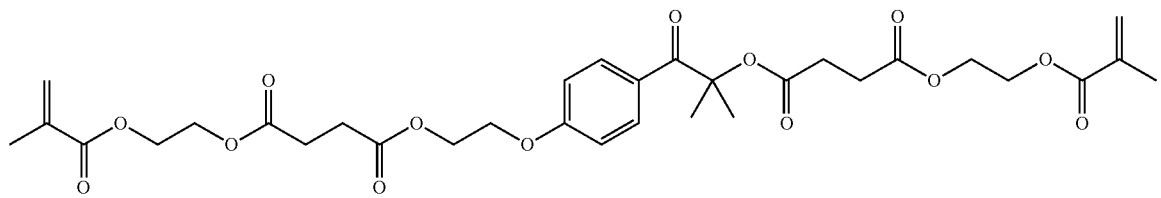

Its feasibility of this approach allows a rapid exploration on its versatility for a new class of resin. Accordingly, a variety of such polymerizable and photocleavable resin monomers were successfully prepared with wide range of viscosity as illustrated in Scheme II.

Scheme II: General Reaction Pathway towards Photopolymerizable and Photocleavable Resin Monomers

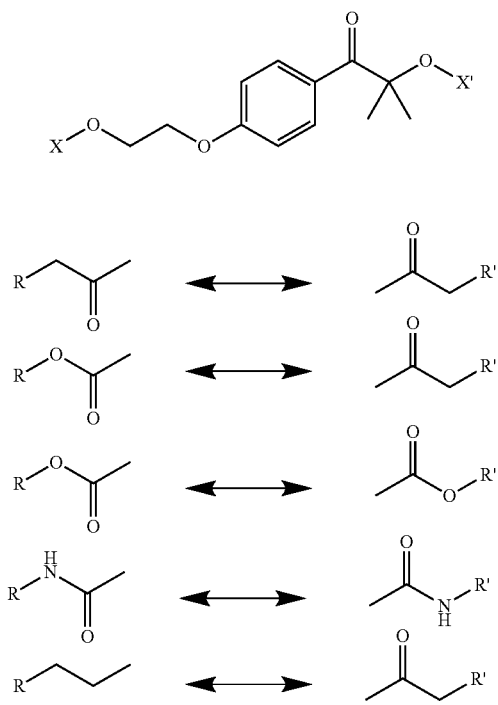

*R, R' are same or different as alkylated (meth)acrylate, amide, vinyl or epoxy groups.

Furthermore, such new resin monomer was formulated with other conventional resin monomers like BisGMA, TEGDMA, UDMA or experimental resin monomer like macrocyclic resin in a variety ratio in order to have overall performance got balanced for the resulting composites. As showed in the following examples, remarkable low shrinkage, low stress and excellent mechanical property plus the good handling characteristics were demonstrated by those composites based on such new class P & P resin monomers.

TABLE I

Polymerization Shrinkage and Stress for Various Activated Resin Mix

| | Shrinkage (%) by Helium Pycnometer | Stress (MPa) by Tensometer |
| --- | --- | --- |
| Denfortex Resin | 10.2 | 4.1 |
| TPH Resin/999446 | 6.8 | 4.5 |
| TPH Resin/999447 | 7.3 | 4.3 |
| Harpoon Resin/XJ5-12 | 5.5 | 3.1 |

TABLE I-continued

Polymerization Shrinkage and Stress for Various Activated Resin Mix

| | Shrinkage (%) by Helium Pycnometer | Stress (MPa) by Tensometer |
| --- | --- | --- |
| Harpoon Resin/XJ5-26 | 5.8 | 3.2 |
| P&P Resin/LB5-158-1 | 5.2 | 1.4 |
| P&P Resin/LB5-158-2 | 5.7 | 2.0 |
| P&P Resin/LB5-158-3 | 6.5 | 1.9 |
| P&P Resin/LB5-158-4 | 6.2 | 1.5 |
| P&P Resin/LB5-158-5 | 6.9 | 1.5 |

TABLE II

Polymerization Shrinkage, Stress and Microstrain for Various Composites

| | Shrinkage (%) by Helium Pycnometer | Microstrain (ue) by Strain Gage | Stress (MPa) by Tensometer |
| --- | --- | --- | --- |
| TPH/A2 | 3.10 | 1600 | 2.9 |
| EstheLX/A2 | 2.92 | 1995 | 2.5 |
| SureFil/A | 2.09 | 1840 | 2.7 |
| Supreme/A2B | 2.65 | 1720 | N/A |
| Supreme/YT | 2.39 | 2005 | N/A |
| Harpoon/A2 | 1.34 | 1000 | 1.7 |
| Harpoon/A3.5 | 1.70 | N/A | 1.8 |
| Harpoon/B1 | 1.31 | N/A | 1.5 |
| Harpoon/B2 | 1.61 | N/A | 1.9 |
| Harpoon/CE | 1.70 | N/A | 1.9 |
| P&P Composite/LB5-156 | 0.87 | N/A | 1.5 |
| P&P Composite/LB5-153 | 0.93 | N/A | 1.4 |
| P&P Composite/LB5-160 | 0.36 | N/A | 1.4 |

According to the present invention there is provided a composition of matter that can be polymerized via an energy source, containing portions within the new composition of matter that are reactive to a second energy source. The invention also provides a composition of matter that can by polymerized via an energy source, containing portions within the new composition of matter that are reactive to a second energy source and that upon activation of the second source of energy, de-polymerize and/or degrade. A composition of matter is also provided that can be polymerized via a first energy source, containing portions within the new composition of matter that are reactive to a second energy source and that upon activation of the second source of energy, de-polymerize and/or degrade without substantially effecting the structural properties of the material polymerized by the first energy source. A further composition of matter is provided that can be polymerized via a first energy source, containing portions within the new composition of matter that are reactive to a second energy source and that upon activation of the second source of energy, de-polymerize and/or degrade to elevate stress created during the polymerization of the composition of matter created via the first energy source without substantially effecting the structural properties of the material polymerized by the first energy source. According to another aspect of the invention, a composition of matter is provided that comprises monomers, prepolymers and/or polymers that can by polymerized via an energy source (thermal, photochemical, chemical, ultrasonic, microwave, etc.), containing portions within the new composition of matter that are reactive to a second energy source (thermal, photochemical, chemical, ultrasonic, microwave, etc.).

Thus, certain limitations of the heretofore known art have been overcome. Polymer networks with cross-linking are desired for strength properties, but lead to higher degree of shrinkage and stress. This invention allows formation of cross-linking, while at the same time, providing a mechanism (the second form of energy application) that relieves the stress created while maintaining the structural integrity of the polymer network created. Relief of stress during polymerization has been desired and typically approached through attempts to relieve stress during the "pre-gel" state of polymerization, prior to the "post-gel" state, wherein the polymer network has now been established, cross-linked set up and, due to the more rigid state, stress is created. The invention substantially eliminates the stress during this "post-gel" state. There are prior known systems for materials that are reversible—that is, once polymerized, some form of postpolymerization energy is applied to fully decompose or degrade the polymer network to a state that renders the material unusable. In the present invention, there is provided only partially, in a controllable manner, degrading or decomposing a portion of the polymer network and maintaining the integrity of the polymer network.

What is claimed is:

1. A polymerized composition having a polymer network formed by activation of a photopolymerizable and photocleavable (P&P) resin monomer using a first energy source, wherein portions of the polymer network are reactive to a second energy source and upon activation of the second source of energy, de-polymerize and/or degrade to elevate stress created during the polymerization of the polymer network created via the first energy source without substantially effecting the structural properties of the polymer network polymerized by the first energy source;

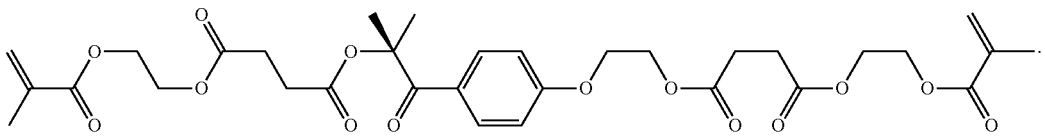

wherein the polymer network is formed by activation of the photopolymerizable and photocleavable (P&P) resin monomer and BisGMA, TEGDMA, or UDMA resin; and wherein the content of the photopolymerizable and photocleavable (P&P) resin monomer is in the range of 20-70% by weight percent;

and wherein the photopolymerizable and photocleavable (P&P) resin monomer is

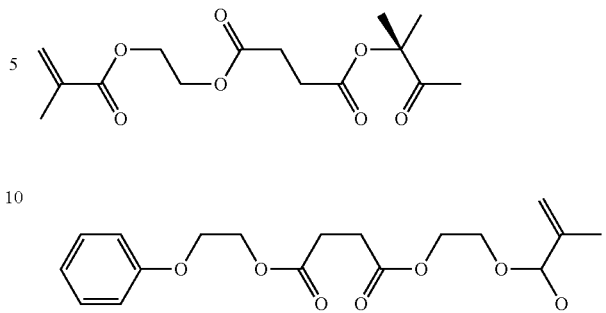

2. The polymerized composition of claim 1, wherein the photopolymerizable and photocleavable (P&P) resin monomer can be a liquid or semicrystalline solid material.

3. The polymerized composition of claim 1, wherein after polymerization, stress ranges from about 1.4 MPa to about 2.0 MPa (by Tensometer).

4. A polymerized composition having a polymer network formed of the process comprising the steps of:

activating a photopolymerizable and photocleavable (P&P) resin monomer using a first energy source to initiate polymerization and form the polymer network;

de-polymerizing and/or degrading a portion of the polymer network upon activation of a second energy source to elevate stress created during the polymerization of the polymer network created via the first energy source without substantially effecting the structural properties of the polymer network polymerized by the first energy source;

wherein after polymerization with selective degradation of the photopolymerizable and photocleavable (P&P) resin monomer using the first and second energy sources, the total stress concentration is reduced while maintaining the structural integrity of the polymer network;

and wherein the photopolymerizable and photocleavable (P&P) resin monomer is

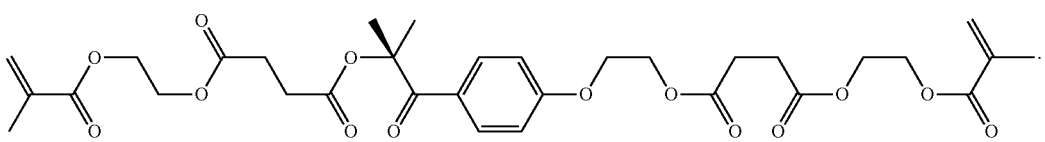

5. The polymerized composition of claim 4, wherein after polymerization, stress ranges from about 1.4 MPa to about 2.0 MPa (by Tensometer).

6. The polymerized composition of claim 1, wherein the polymer network is selectively degraded using the second energy source during a post-gel stage of polymerization.

7. The polymerized composition of claim 4, wherein the polymer network is selectively degraded using the second energy source during a post-gel stage of polymerization.

* * * * *